United States Patent [19]

Wu et al.

[11] Patent Number: 5,981,830
[45] Date of Patent: Nov. 9, 1999

[54] KNOCKOUT MICE AND THEIR PROGENY WITH A DISRUPTED HEPSIN GENE

[75] Inventors: Qingyu Wu, El Sobrante, Calif.; Jasper E. Sadler, St. Louis, Mo.

[73] Assignees: Schering Aktiengesellschaft, Berlin, Germany; Washington University, St. Louis, Mo.

[21] Appl. No.: 09/000,846

[22] Filed: Dec. 30, 1997

Related U.S. Application Data

[63] Continuation-in-part of application No. 08/866,058, May 30, 1997, abandoned.
[51] Int. Cl.$^6$ .......................... C12N 15/09; C12N 15/63; C12N 15/00; C12N 5/00
[52] U.S. Cl. .................. 800/18; 800/21; 800/22; 800/25; 800/3; 435/455; 435/463; 435/320.1; 435/325; 530/350; 526/23.5
[58] Field of Search ................. 800/18, 21, 22, 800/25, 3; 435/455, 463, 320.1, 325; 530/350; 526/23.5

[56] References Cited

PUBLICATIONS

Leytus et al., "A Novel Trypsin–like Serine Protease (Hepsin) with a Putative Transmembrane Domain Expressed by Human Liver and Hepatoma Cells", *Biochemistry*, vol. 27, pp. 1067–1074, 1988.

Kazama et al., "Hepsin, a Putative Membrane–associated Serine Protease, Activates Human Factor VII and Initiates a Pathway of Blood Coagulation on the Cell Surface Leading to Thrombin Formation",*J. of Biol. Chem.*, 270(1):66–72, 1995.

Torres–Rosado et al., "Hepsin, a putative cell–surface protease, is required for mammalian cell growth", *Proc. Natl. Acad. Sci.*USA, vol. 90, pp. 7181–7185, Aug. 1993.

Capecchi, *Scientific American*, 270(3):34–41.

Darrow et al., *Thrombosis and Haemostasis*, 76(6):860–866.

*Primary Examiner*—Brian R. Stanton
*Assistant Examiner*—Jill D. Martin
*Attorney, Agent, or Firm*—Millen, White, Zelano & Branigan, P.C.

[57] ABSTRACT

The present invention provides a transgenic mouse comprising a disrupted hepsin gene. In particular, the invention provides methods of making the transgenic mouse comprising the disrupted hepsin gene by utilizing a hepsin targeting vector for homologous recombination in mouse embryonic stem cells. Also, nucleotide and amino acid hepsin sequences are disclosed.

17 Claims, 4 Drawing Sheets

```
GTCAACCTGGGAATCATTAACAAGAGTCCCTGACATGGCGAAGGAGGGTGGCCGGACTGC
                                  M   A   K   E   G   G   R   T   A

AGCATGCTGCTCCAGACCCAAGGTGGCAGCTCTCATTGTGGGTACCCTGCTGTTCCTGAC
 A   C   C   S   R   P   K   V   A   A   L   I   V   G   T   L   L   F   L   T

AGGCATTGGGGCCGCGTCCTGGGCCATTGTGACCATCCTACTGCAGAGTGACCAGGAGCC
 G   I   G   A   A   S   W   A   I   V   T   I   L   L   Q   S   D   Q   E   P

ACTGTACCAAGTGCAGCTCAGTCCAGGGGACTCACGGCTTGCGGTGTTTGACAAGACGGA
 L   Y   Q   V   Q   L   S   P   G   D   S   R   L   A   V   F   D   K   T   E

GGGAACGTGGAGGCTACTGTGCTCCTCACGCTCCAATGCCAGGGTGGCAGGGCTCGGCTG
 G   T   W   R   L   L   C   S   S   R   S   N   A   R   V   A   G   L   G   C

TGAGGAGATGGGCTTTCTCAGGGCTCTGGCGCACTCGGAGCTGGATGTCCGCACTGCGGG
  E   E   M   G   F   L   R   A   L   A   H   S   E   L   D   V   R   T   A   G

CGCCAACGGCACATCGGGCTTCTTTTGCGTGGACGAGGGCGGACTCCGTCTGGCTCAGAG
 A   N   G   T   S   G   F   F   C   V   D   E   G   G   L   R   L   A   Q   R

GTTGCTGGATGTCATCTCTGTATGTGACTGTCCTAGAGGCCGATTCCTGACTGCCACCTG
 L   L   D   V   I   S   V   C   D   C   P   R   G   R   F   L   T   A   T   C

CCAAGACTGTGGCCGCAGGAAGCTGCCGGTGGACCGCATTGTGGGGGGCCAGGACAGCAG
 Q   D   C   G   R   R   K   L   P   V   D   R   I   V   G   G   Q   D   S   S

TCTGGGAAGGTGGCCGTGGCAGGTCAGCCTGCGTTATGATGGGACCCACCTCTGTGGGGG
 L   G   R   W   P   W   Q   V   S   L   R   Y   D   G   T   H   L   C   G   G

GTCCCTGCTGTCTGGGGACTGGGTGCTGACTGCTGCACATTGCTTTCCAGAGCGGAACCG
 S   L   L   S   G   D   W   V   L   T   A   A   H   C   F   P   E   R   N   R

GGTCCTGTCTCGGTGGCGAGTATTTGCTGGTGCTGTAGCCCGGACCTCACCCCATGCTGT
 V   L   S   R   W   R   V   F   A   G   A   V   A   R   T   S   P   H   A   V

GCAACTGGGGGTTCAGGCTGTGATCTATCATGGGGGCTACCTTCCCTTTCGAGACCCTAC
 Q   L   G   V   Q   A   V   I   Y   H   G   G   Y   L   P   F   R   D   P   T

TATCGACGAAAACAGCAATGACATTGCCTTGGTCCACCTCTCTAGCTCCCTGCCTCTCAC
 I   D   E   N   S   N   D   I   A   L   V   H   L   S   S   S   L   P   L   T

AGAATACATCCAGCCAGTGTGTCTCCCTGCTGCGGGACAGGCCCTGGTGGATGGCAAGGT
 E   Y   I   Q   P   V   C   L   P   A   A   G   Q   A   L   V   D   G   K   V

CTGTACTGTGACCGGCTGGGGTAACACACAGTTCTATGGCCAACAGGCTATGGTGCTCCA
   C   T   V   T   G   W   G   N   T   Q   F   Y   G   Q   Q   A   M   V   L   Q

AGAGGCCCGGGTTCCCATCATAAGCAACGAAGTTTGCAACAGCCCCGACTTCTACGGGAA
 E   A   R   V   P   I   I   S   N   E   V   C   N   S   P   D   F   Y   G   N

TCAGATCAAGCCCAAGATGTTCTGTGCTGGCTATCCTGAGGGTGGCATTGATGCGTGCCA
 Q   I   K   P   K   M   F   C   A   G   Y   P   E   G   G   I   D   A   C   Q

GGGCGACAGTGGAGGCCCCTTTGTGTGTGAAGACAGCATCTCTGGGACATCAAGGTGGCG
 G   D   S   G   G   P   F   V   C   E   D   S   I   S   G   T   S   R   W   R

GCTATGTGGCATTGTAAGCTGGGGTACGGGCTGTGCTTTGGCCCGGAAGCCAGGAGTGTA
   L   C   G   I   V   S   W   G   T   G   C   A   L   A   R   K   P   G   V   Y

CACCAAAGTCACTGACTTCCGGGAGTGGATCTTCAAGGCCATAAAGACTCACTCCGAAGC
 T   K   V   T   D   F   R   E   W   I   F   K   A   I   K   T   H   S   E   A

CAGTGGCATGGTGACTCAGCCCTGATCCCGCCTCATCTCGCTGCTCCGTGCTGCACTAGC
   S   G   M   V   T   Q   P   *

ATCCAGAGTCAGAGTTGGTCTGGTGGCTCCAGCCCCACGTGGTAGGCTCCACACTGGGCC
TCACATGGAATGGTTTCCTGCTCAGATCCAGTCCACGGGTCCAAGGATGCTGGATCCAAG
GACTTCTCTTCCACAGTGGCCGGCCCACTCAATCCCAGGGCCATTGGCCTCACCCTCCCA
CCCCATGTAAATATTACTCTGTCCTCTGGGGGGCGCTCTAGGGAGCCCTTGTGCAGATGC
TCTTTAAATAATAAAGGTGGTTTTTGATTAAAAAAAAAAAAAAAAAAA
```

FIG. 2

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1605 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Mus musculus (ix) FEATURE:
      (A) NAME/KEY: CDS
      (B) LOCATION: 35..1282

(xi) SEQUENCE DESCRIPTION: SEQ ID NO:1:

```
GTCAACCTGG GAATCATTAA CAAGAGTCCC TGAC ATG GCG AAG GAG GGT GGC           52
                                     Met Ala Lys Glu Gly Gly
                                      1               5

CGG ACT GCA GCA TGC TGC TCC AGA CCC AAG GTG GCA GCT CTC ATT GTG        100
Arg Thr Ala Ala Cys Cys Ser Arg Pro Lys Val Ala Ala Leu Ile Val
         10                  15                  20

GGT ACC CTG CTG TTC CTG ACA GGC ATT GGG GCC GCG TCC TGG GCC ATT        148
Gly Thr Leu Leu Phe Leu Thr Gly Ile Gly Ala Ala Ser Trp Ala Ile
             25                  30                  35

GTG ACC ATC CTA CTG CAG AGT GAC CAG GAG CCA CTG TAC CAA GTG CAG        196
Val Thr Ile Leu Leu Gln Ser Asp Gln Glu Pro Leu Tyr Gln Val Gln
     40                  45                  50

CTC AGT CCA GGG GAC TCA CGG CTT GCG GTG TTT GAC AAG ACG GAG GGA        244
Leu Ser Pro Gly Asp Ser Arg Leu Ala Val Phe Asp Lys Thr Glu Gly
 55                  60                  65                  70

ACG TGG AGG CTA CTG TGC TCC TCA CGC TCC AAT GCC AGG GTG GCA GGG        292
Thr Trp Arg Leu Leu Cys Ser Ser Arg Ser Asn Ala Arg Val Ala Gly
                 75                  80                  85
```

| | | |
|---|---|---|
| CTC GGC TGT GAG GAG ATG GGC TTT CTC AGG GCT CTG GCG CAC TCG GAG<br>Leu Gly Cys Glu Glu Met Gly Phe Leu Arg Ala Leu Ala His Ser Glu<br>90                                         95                                100 | | 340 |
| CTG GAT GTC CGC ACT GCG GGC GCC AAC GGC ACA TCG GGC TTC TTT TGC<br>Leu Asp Val Arg Thr Ala Gly Ala Asn Gly Thr Ser Gly Phe Phe Cys<br>             105                                 110                              115 | | 388 |
| GTG GAC GAG GGC GGA CTC CGT CTG GCT CAG AGG TTG CTG GAT GTC ATC<br>Val Asp Glu Gly Gly Leu Arg Leu Ala Gln Arg Leu Leu Asp Val Ile<br>120                                    125                                 130 | | 436 |
| TCT GTA TGT GAC TGT CCT AGA GGC CGA TTC CTG ACT GCC ACC TGC CAA<br>Ser Val Cys Asp Cys Pro Arg Gly Arg Phe Leu Thr Ala Thr Cys Gln<br>135                             140                             145                           150 | | 484 |
| GAC TGT GGC CGC AGG AAG CTG CCG GTG GAC CGC ATT GTG GGG GGC CAG<br>Asp Cys Gly Arg Arg Lys Leu Pro Val Asp Arg Ile Val Gly Gly Gln<br>                     155                               160                           165 | | 532 |
| GAC AGC AGT CTG GGA AGG TGG CCG TGG CAG GTC AGC CTG CGT TAT GAT<br>Asp Ser Ser Leu Gly Arg Trp Pro Trp Gln Val Ser Leu Arg Tyr Asp<br>                 170                               175                           180 | | 580 |
| GGG ACC CAC CTC TGT GGG GGG TCC CTG CTG TCT GGG GAC TGG GTG CTG<br>Gly Thr His Leu Cys Gly Gly Ser Leu Leu Ser Gly Asp Trp Val Leu<br>                       185                              190                           195 | | 628 |
| ACT GCT GCA CAT TGC TTT CCA GAG CGG AAC CGG GTC CTG TCT CGG TGG<br>Thr Ala Ala His Cys Phe Pro Glu Arg Asn Arg Val Leu Ser Arg Trp<br>200                                  205                             210 | | 676 |
| CGA GTA TTT GCT GGT GCT GTA GCC CGG ACC TCA CCC CAT GCT GTG CAA<br>Arg Val Phe Ala Gly Ala Val Ala Arg Thr Ser Pro His Ala Val Gln<br>215                             220                             225                         230 | | 724 |
| CTG GGG GTT CAG GCT GTG ATC TAT CAT GGG GGC TAC CTT CCC TTT CGA<br>Leu Gly Val Gln Ala Val Ile Tyr His Gly Gly Tyr Leu Pro Phe Arg<br>                             235                             240                           245 | | 772 |
| GAC CCT ACT ATC GAC GAA AAC AGC AAT GAC ATT GCC TTG GTC CAC CTC<br>Asp Pro Thr Ile Asp Glu Asn Ser Asn Asp Ile Ala Leu Val His Leu<br>                     250                             255                         260 | | 820 |
| TCT AGC TCC CTG CCT CTC ACA GAA TAC ATC CAG CCA GTG TGT CTC CCT<br>Ser Ser Ser Leu Pro Leu Thr Glu Tyr Ile Gln Pro Val Cys Leu Pro<br>                 265                               270                           275 | | 868 |
| GCT GCG GGA CAG GCC CTG GTG GAT GGC AAG GTC TGT ACT GTG ACC GGC<br>Ala Ala Gly Gln Ala Leu Val Asp Gly Lys Val Cys Thr Val Thr Gly<br>280                                  285                             290 | | 916 |
| TGG GGT AAC ACA CAG TTC TAT GGC CAA CAG GCT ATG GTG CTC CAA GAG<br>Trp Gly Asn Thr Gln Phe Tyr Gly Gln Gln Ala Met Val Leu Gln Glu<br>295                                  300                             305                         310 | | 964 |
| GCC CGG GTT CCC ATC ATA AGC AAC GAA GTT TGC AAC AGC CCC GAC TTC<br>Ala Arg Val Pro Ile Ile Ser Asn Glu Val Cys Asn Ser Pro Asp Phe<br>                     315                               320                           325 | | 1012 |
| TAC GGG AAT CAG ATC AAG CCC AAG ATG TTC TGT GCT GGC TAT CCT GAG<br>Tyr Gly Asn Gln Ile Lys Pro Lys Met Phe Cys Ala Gly Tyr Pro Glu<br>                     330                             335                           340 | | 1060 |
| GGT GGC ATT GAT GCG TGC CAG GGC GAC AGT GGA GGC CCC TTT GTG TGT<br>Gly Gly Ile Asp Ala Cys Gln Gly Asp Ser Gly Gly Pro Phe Val Cys<br>                 345                               350                           355 | | 1108 |
| GAA GAC AGC ATC TCT GGG ACA TCA AGG TGG CGG CTA TGT GGC ATT GTA<br>Glu Asp Ser Ile Ser Gly Thr Ser Arg Trp Arg Leu Cys Gly Ile Val<br>360                                  365                             370 | | 1156 |
| AGC TGG GGT ACG GGC TGT GCT TTG GCC CGG AAG CCA GGA GTG TAC ACC<br>Ser Trp Gly Thr Gly Cys Ala Leu Ala Arg Lys Pro Gly Val Tyr Thr<br>375                             380                             385                         390 | | 1204 |
| AAA GTC ACT GAC TTC CGG GAG TGG ATC TTC AAG GCC ATA AAG ACT CAC<br>Lys Val Thr Asp Phe Arg Glu Trp Ile Phe Lys Ala Ile Lys Thr His<br>                     395                             400                         405 | | 1252 |

```
TCC GAA GCC AGT GGC ATG GTG ACT CAG CCC TGATCCCGCC TCATCTCGCT      1302
Ser Glu Ala Ser Gly Met Val Thr Gln Pro
        410                 415

GCTCCGTGCT GCACTAGCAT CCAGAGTCAG AGTTGGTCTG GTGGCTCCAG CCCCACGTGG  1362

TAGGCTCCAC ACTGGGCCTC ACATGGAATG GTTTCCTGCT CAGATCCAGT CCACGGGTCC  1422

AAGGATGCTG GATCCAAGGA CTTCTCTTCC ACAGTGGCCG GCCCACTCAA TCCCAGGGCC  1482

ATTGGCCTCA CCCTCCCACC CCATGTAAAT ATTACTCTGT CCTCTGGGGG GCGCTCTAGG  1542

GAGCCCTTGT GCAGATGCTC TTTAAATAAT AAAGGTGGTT TTGATTAAAA AAAAAAAAA   1602

AAA                                                                1605

(2) INFORMATION FOR SEQ ID NO:2:

(i) SEQUENCE CHARACTERISTICS:
        (A) LENGTH: 416 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Lys Glu Gly Gly Arg Thr Ala Ala Cys Cys Ser Arg Pro Lys
 1               5                  10                  15

Val Ala Ala Leu Ile Val Gly Thr Leu Leu Phe Leu Thr Gly Ile Gly
            20                  25                  30

Ala Ala Ser Trp Ala Ile Val Thr Ile Leu Leu Gln Ser Asp Gln Glu
        35                  40                  45

Pro Leu Tyr Gln Val Gln Leu Ser Pro Gly Asp Ser Arg Leu Ala Val
    50                  55                  60

Phe Asp Lys Thr Glu Gly Thr Trp Arg Leu Leu Cys Ser Ser Arg Ser
65                  70                  75                  80

Asn Ala Arg Val Ala Gly Leu Gly Cys Glu Glu Met Gly Phe Leu Arg
                85                  90                  95

Ala Leu Ala His Ser Glu Leu Asp Val Arg Thr Ala Gly Ala Asn Gly
            100                 105                 110

Thr Ser Gly Phe Phe Cys Val Asp Glu Gly Gly Leu Arg Leu Ala Gln
        115                 120                 125

Arg Leu Leu Asp Val Ile Ser Val Cys Asp Cys Pro Arg Gly Arg Phe
130                 135                 140

Leu Thr Ala Thr Cys Gln Asp Cys Gly Arg Arg Lys Leu Pro Val Asp
145                 150                 155                 160

Arg Ile Val Gly Gly Gln Asp Ser Ser Leu Gly Arg Trp Pro Trp Gln
                165                 170                 175

Val Ser Leu Arg Tyr Asp Gly Thr His Leu Cys Gly Gly Ser Leu Leu
            180                 185                 190

Ser Gly Asp Trp Val Leu Thr Ala Ala His Cys Phe Pro Glu Arg Asn
        195                 200                 205

Arg Val Leu Ser Arg Trp Arg Val Phe Ala Gly Ala Val Ala Arg Thr
    210                 215                 220

Ser Pro His Ala Val Gln Leu Gly Val Gln Ala Val Ile Tyr His Gly
225                 230                 235                 240

Gly Tyr Leu Pro Phe Arg Asp Pro Thr Ile Asp Glu Asn Ser Asn Asp
                245                 250                 255

Ile Ala Leu Val His Leu Ser Ser Ser Leu Pro Leu Thr Glu Tyr Ile
            260                 265                 270

Gln Pro Val Cys Leu Pro Ala Ala Gly Gln Ala Leu Val Asp Gly Lys
```

```
                    275                 280                 285
       Val Cys Thr Val Thr Gly Trp Gly Asn Thr Gln Phe Tyr Gly Gln Gln
           290                 295                 300

Ala Met Val Leu Gln Glu Ala Arg Val Pro Ile Ile Ser Asn Glu Val
       305                 310                 315                 320

Cys Asn Ser Pro Asp Phe Tyr Gly Asn Gln Ile Lys Pro Lys Met Phe
                       325                 330                 335

Cys Ala Gly Tyr Pro Glu Gly Gly Ile Asp Ala Cys Gln Gly Asp Ser
                       340                 345                 350

Gly Gly Pro Phe Val Cys Glu Asp Ser Ile Ser Gly Thr Ser Arg Trp
                       355                 360                 365

Arg Leu Cys Gly Ile Val Ser Trp Gly Thr Gly Cys Ala Leu Ala Arg
                       370                 375                 380

Lys Pro Gly Val Tyr Thr Lys Val Thr Asp Phe Arg Glu Trp Ile Phe
       385                 390                 395                 400

Lys Ala Ile Lys Thr His Ser Glu Ala Ser Gly Met Val Thr Gln Pro
                       405                 410                 415
```

(2) INFORMATION FOR SEQ ID NO:3:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "SENSE PRIMER"

(iii) HYPOTHETICAL: NO (iv) ANTI-SENSE: NO (xi) SEQUENCE DESCRIPTION: SEQ ID NO:3:

TTCGCCATCT GCCAAGACTG                                               20

(2) INFORMATION FOR SEQ ID NO:4:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "ANTISENSE PRIMER"

(iii) HYPOTHETICAL: NO (iv) ANTI-SENSE: YES (xi) SEQUENCE DESCRIPTION: SEQ ID NO:4:

GTGAGTCTTT ATGGCCTGGA AGAT                                         24

(2) INFORMATION FOR SEQ ID NO:5:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "SENSE PRIMER"

(iii) HYPOTHETICAL: NO

-continued

```
    (iv) ANTI-SENSE: NO (xi) SEQUENCE DESCRIPTION: SEQ ID NO:5:

CAAGATGGAT TGCACGCAGG                                            20

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ANTISENSE PRIMER"

(iii) HYPOTHETICAL: NO (iv) ANTI-SENSE: YES (xi) SEQUENCE DESCRIPTION: SEQ ID NO:6:

GTAAAGCACG AGGAAGCGG                                             19

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SENSE PRIMER"

(iii) HYPOTHETICAL: NO (iv) ANTI-SENSE: NO (xi) SEQUENCE DESCRIPTION: SEQ ID NO:7:

ACGGCACATC GGGCTTCTTT T                                          21

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "ANTISENSE PRIMER"

(iii) HYPOTHETICAL: NO (iv) ANTI-SENSE: YES (xi) SEQUENCE DESCRIPTION: SEQ ID NO:8:

ATTGCGGTCC ACCGGCAGCT TCCT                                       24
```

KNOCKOUT MICE AND THEIR PROGENY WITH A DISRUPTED HEPSIN GENE

This application is a continuation-in-part of application U.S. Ser. No. 008/866,058, filed May 30, 1997, now abandoned.

BACKGROUND OF THE INVENTION

Proteases participate in a variety of developmental and metabolic processes (Stroud R, *Sci. Am.* 231:74–88 (1974) and Neurath H, *Science* 224:350–357 (1984). Molecular defects that alter enzyme function often lead to serious human diseases, such as bleeding, thrombosis, and atherosclerosis. Hepsin is a novel serine protease of the trypsin family and contains a transmembrane domain near its amino-terminus, Kurachi et al., *Methods in Enzymology*, 244:100–114 (1994). This structural feature distinguishes hepsin from most other serine proteases. In the fruitfly *Drosophila melanogaster*, another transmembrane serine protease, Stubble-stubbloid, has been reported that has similar structural features as that of hepsin. Stubble-stubbloid protein plays an important role in epithelial morphogenesis and development in Drosophila. Defects in Stubble-stubbloid gene cause malformation of legs, wings and bristles, Appel et al., *Proc. Natl. Acad. Sci. USA* 90:4937–4941 (1993).

The human hepsin cDNA was initially isolated from a liver cDNA library screened with a mixture of oligonucleotides based on a consensus sequence of serine proteases, Leytus et al., *Biochemistry* 27:1067–1074 (1988). Biochemical studies indicate that hepsin is a type II transmembrane serine protease expressed mainly on the surface of hepatocytes, Tsugi et al., *J. Biol. Chem.* 266:16948–16953 (1991). Lower levels of hepsin mRNA are detected in other tissues including lung, kidney, pancreas, stomach, thyroid and prostate. In addition, hepsin mRNA is present in several human tumor cell lines, such as hepatoma cells HepG2 and PLC/PRF/5, mammary cancer cells MCF784 and T470, and epitheloid carcinoma cells HeLa S3, Tsuji et al., *J. Biol. Chem.* 266:16948–16953 (1991) and Torres-Rosado et al., *Proc. Natl. Acad. Sci. USA* 90:7181–7185 (1993).

Hepsin has a number of reported activities. In an in vitro study, recombinant human hepsin expressed on the cell surface activated blood coagulation factor VII but not factors IX, X, prothrombin or protein C, all of which share significant structural and sequence similarities with factor VII. The activation of factor VII by hepsin was shown to be sufficient to initiate the coagulation pathway leading to thrombin formation, Kazama et al., *J. Biol. Chem.* 270:66–72 (1995). Elevated plasma factor VIIa activity has been known to be a significant risk factor for ischemic heart disease and cardiovascular death, Hultin, *Prog. Hemostasis Thrombosis* 10:215–241, (1991) and Mann, *Arteriosclerosis* 9:783–784 (1989). Factor VIIa/tissue factor complex also contributes to tumor-related hypercoagulability and intravascular thrombosis, Edwards et al., *Thromb. Haemostasis* 69:205–213 (1993).

In addition to blood coagulation, hepsin was reported to be critical for cell growth. In a cell culture system, addition of anti-hepsin antibodies or hepsin-specific antisense oligonucleotides to the culture medium significantly inhibited growth of hepatoma cells Torres-Rosado et al., *Proc. Natl. Acad. Sci. USA*, 90:7181–7185 (1993). This observation is quite interesting in light of the expression of hepsin mRNA in a number of tumor cells. The growth factor-like activities of serine proteases have been known for many years. For example, thrombin is a potent mitogen for vascular fibroblasts and smooth muscle cells, Fenton J, *Ann. N.Y. Acad. Sci.*, 485:5–15 (1986). Furthermore, serine proteases also participate in processing of growth factors, Massague J, *J. Biol. Chem.*, 265:21393–21396 (1990). The hepsin-dependent tumor cell growth indicates a mechanism in which hepsin functions either directly as a growth factor or indirectly as an enzyme that processes certain growth factors essential for cell growth.

DESCRIPTION OF THE DRAWINGS

FIG. 2 shows a full-length cDNA (SEQ ID NO: 1) and amino acid (SEQ ID NO:2) coding sequence for a mouse hepsin gene.

DESCRIPTION OF THE INVENTION

Figure 1A:
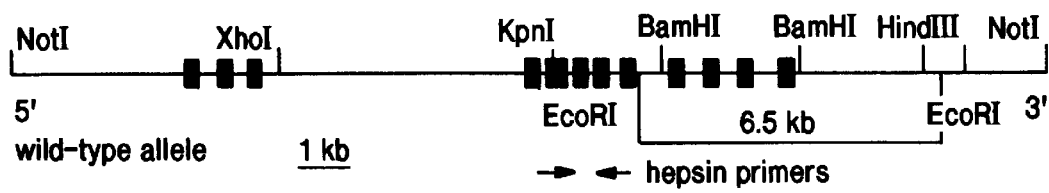
FIGS. 1(A–C) shows a wild-type mouse hepsin gene (A), a targeting vector (B) designed to target the mouse hepsin gene, and a modified mouse hepsin gene (C) which has been modified by the targeting vector.

The present invention relates to a serine protease, especially hepsin, and a nucleic acid coding for it. In one aspect, the invention provides a mammalian cell in which expression of a gene coding for a serine protease, especially hepsin, has been "knocked out" or disrupted. In a preferred embodiment, disruption of the serine protease gene, e.g., a hepsin gene, is achieved by the insertion of a nucleotide sequence into it which is effective to suppress the gene's expression.

The invention especially relates to a mammal containing one or more cells in which expression of the serine protease gene is functionally inactivated or disrupted. Functional inactivation or disruption refers, e.g., to a partial or complete reduction of the expression of at least a portion of a polypeptide encoded by an endogenous serine protease gene of a single cell, selected cells, or all of the cells of a mammal. The term "knockout" is a synonym for functional inactivation of the gene.

In one embodiment, a gene targeting strategy is utilized that facilitates the introduction of a desired nucleotide sequence into a serine protease gene, preferably a hepsin gene. The gene targeting strategy preferably utilizes double reciprocal recombination and a positive selectable marker to assist in the insertion of the nucleotide sequence into a target nucleic acid. The target nucleic acid is preferably a gene, more preferably a gene at its particular chromosomal locus. The desired nucleotide sequence is inserted into the gene in such a way that the gene is functionally disrupted, i.e., its expression is partially or completely reduced.

In one aspect of the invention, a targeting vector is employed to insert a selectable marker into a predefined position of a gene, preferably a serine protease such as hepsin. The position is selected to achieve functional disruption of the gene upon insertion of the selectable marker. For such purposes, a preferred embodiment is a recombinant nucleic acid molecule comprising: (1) a 5' nucleotide sequence which is effective to achieve homologous recombination at a first predefined position of a mammalian serine protease gene, e.g., hepsin, operably linked to (2) the 5' terminus of a first selectable nucleotide sequence which confers a first selection characteristic on a cell in which it is present, and (3) a 3' nucleotide sequence which is effective to achieve homologous recombination at a second predefined position of the mammalian serine protease gene, e.g., hepsin gene, operably linked to the 3' terminus of the first selectable nucleotide sequence. The recombinant nucleic acid molecule is effective to achieve homologous recombination in a mammalian chromosome at predefined location. Fragments of the targeting vector are also within the scope of the invention, e.g., recombinant nucleic acid molecules comprising elements (1) and (2), or comprising elements (2) and (3), etc.

The term recombinant refers, e.g., to a nucleic acid molecule which has been modified by the hand-of-man, e.g., comprising fragments of nucleic acid from different sources or a nucleic acid molecule from one source which has been engineered. Thus, the nucleic acid molecule is recombinant, e.g., because it comprises nucleotide sequences from a mammalian hepsin gene and selectable marker gene. A molecule is also recombinant when it contains sequences from the same gene but arranged in a manner that does not occur in nature, i.e., a non-naturally-occurring arrangement.

Homologous recombination refers to the process in which nucleic acid molecules with similar genetic information line up side-by-side and exchange nucleotide strands. A nucleotide sequence of the recombinant nucleic acid which is effective to achieve homologous recombination at a predefined position of a target nucleic acid therefore indicates a nucleotide sequence which facilitates the exchange of nucleotide strands between the recombinant nucleic acid molecule at a defined position of a target gene, e.g., a mouse hepsin gene. The effective nucleotide sequence generally comprises a nucleotide sequence which is complementary to a desired target nucleic acid molecule (e.g., the gene locus to be modified), promoting nucleotide base pairing. Any nucleotide sequence can be employed as long as it facilitates homologous recombination at a specific and selected position along the target nucleic acid molecule. Generally, there is an exponential dependence of targeting efficiency on the extent or length of homology between the targeting vector and the target locus. Selection and use of sequences effective for homologous recombination is described, e.g., in Deng and Capecchi, *Mol. Cell. Bio.*, 12:3365–3371, 1992; Bollag et al., *Annu. Rev. Genet.*, 23:199–225, 1989; Waldman and Liskay, *Mol. Cell. Bio.*, 8:5350–5357, 1988.

An aspect of the present invention is to suppress or functionally disrupt expression of a serine protease gene. The phrases "disruption of the gene", "gene disruption," "suppressing expression," "gene suppression," "functional inactivation of the gene," or "functional gene inactivation" refer to modification of the gene in manner which decreases or prevents expression of that gene and/or its product in a cell. The expression of the gene's product can be completely or only partially suppressed, e.g., reduced by 70%, 80%, 85%, 90%, 95%, 99%, or more. A functionally disrupted gene, e.g., a functionally disrupted hepsin gene, includes a modified gene which expresses a truncated polypeptide having less than the entire coding sequence of the wild-type gene. Such a gene is illustrated in the examples below. See, e.g., FIG. 1. A gene can also be functionally disrupted by affecting its mRNA structure in such a way to create an untranslatable message, e.g., frame-shift, decreased stability, etc.

In accordance with the present invention, a serine protease gene is modified in such a manner which is effective to disrupt expression of the corresponding gene product. Thus, e.g., a functionally disrupted recombinant hepsin gene does not express a functional hepsin polypeptide or expresses a functional hepsin polypeptide at levels which are less than wild-type levels of hepsin, e.g., reduced by 70%, 80%, 85%, 90%, 95%, 99%, or more. By "not functional" or "functionally inactive" hepsin polypeptide, it is meant, e.g., that the hepsin is not enzymatically operational. See, Background for a description of hepsin enzymatic activity. The gene can be modified in any effective position, e.g., enhancers, promoters, regulatory regions, noncoding sequences, coding sequences, introns, exons, etc., so as to decrease or prevent expression of that gene in the cell. Insertion into a region of a serine protease gene, e.g., a murine hepsin gene, is usually accomplished by homologous recombination. A recombinant nucleic acid molecule comprising regions of gene homology and a nucleotide sequence coding for a selectable marker gene is inserted into the promoter and/or coding region and/or noncoding regions of a serine protease, whereby expression of the gene is functionally disrupted. When this knockout construct is then inserted into a cell, the construct can integrate into the genomic DNA. Thus, progeny of the cell will only express only one functional copy of the gene; the other copy will no longer express the gene product, or will express it at a decreased level, as the endogenous nucleotide sequence of the gene is now disrupted by the inserted nucleotide sequence. If desired the functional gene can be inactivated in a second analogous step.

Figure 1B:
Figure 1C:
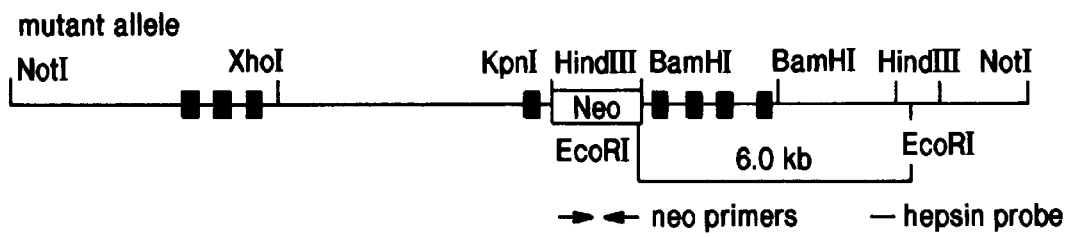

The nucleotide sequence effective for homologous recombination is operably linked to a nucleotide sequence, preferably a selectable marker nucleotide sequence or gene, which is to be inserted into the desired target nucleic acid. For example, an aspect of the present invention is to replace all or part of the nucleotide coding sequence for a hepsin polypeptide of the mouse hepsin gene with a nucleotide sequence for a selectable marker. In the examples, exons 5–8 of the mouse hepsin gene are replaced by a gene coding for neomycin resistance. Its introduction into the gene is achieved by attaching a part of the mouse hepsin gene comprising exon 4 to the 5' terminus of a neomycin resistance gene and a part of the mouse hepsin gene comprising exons 9–12 to the 3' terminus of the selectable marker to form a targeting vector. The mouse hepsin gene segments are positioned with respect to the selectable marker gene in a way such that homologous recombination between them and the mouse gene will result in replacement of mouse exons 5–8 with the selectable marker gene. Such positioning, i.e., operable linkage, means that the mouse gene segment is joined to the selectable marker gene whereby the homologous recombination function can be accomplished. A recombinant nucleic acid molecule of the present invention is effective for disrupting expression of a mammalian gene, preferably a mammalian hepsin gene, such as a murine hepsin gene. This means, e.g., that the molecule comprises sequences effective for homologous recombination into the desired nucleic acid target and that modification of the target by the effective molecule results in a modified target in which expression of the gene product is disrupted. FIG. 1 shows an example of a targeting vector which is effective for disrupting expression of a murine hepsin gene.

The recombinant nucleic acid is preferably inserted into a cell with chromosomal DNA that contains the endogenous gene to be knocked out. In the cell, the recombinant nucleic acid molecule can integrate by homologous recombination with the DNA of the cell in such a position so as to prevent or interrupt transcription of the gene to be knocked out. Such insertion usually occurs by homologous recombination (i.e., regions of the targeting vector that are homologous or complimentary to endogenous DNA sequences hybridize to each other when the targeting vector is inserted into the cell; these regions can then recombine so that part of the targeting vector is incorporated into the corresponding position of the endogenous DNA).

As discussed, one or more nucleotide sequences can be inserted into a serine protease gene to suppress its expression. It is desirable to detect the presence of the nucleotide sequence in the gene. Such detection can be accomplished in various ways, including by nucleic acid hybridization, antibody binding to an epitope encoded by the inserted nucleic acid, or by selection for a phenotype of the inserted sequence. Accordingly, such an inserted nucleotide sequence can be referred to as a first selectable nucleotide sequence. A first selectable nucleotide sequence preferably confers a first selection characteristic on a cell in which it is present. By the phrase "selection characteristic," it is meant, e.g., a characteristic which is expressed in a cell and which can be chosen in preference to another or other characteristics. The selectable nucleotide sequence, also known as selectable marker gene, can be any nucleic acid molecule that is detectable and/or assayable after it has been incorporated into the genomic DNA of the mammal. The selection characteristic can be a positive characteristic, i.e., a characteristic which is expressed or acquired by cells and whose presence enables selection of such cells. A positive selection characteristic can enable survival of the cell or organism, e.g., antibiotic resistance, ouabain-resistance (a gene for a ouabain-resistant sodium/potassium ATPase protein). Examples of positive selection characteristics and a corresponding selection agent include, e.g., Neo and G418 or kanomycin; Hyg and hygromycin, hisD and histidinol; Gpt and xanthine; Ble and bleomycin; Hprt and hypoxanthine. See, e.g., U.S. Pat. No. 5,464,764 and Capecchi, Science, 244:1288–1292, 1989. The presence of the selectable gene in the targeted sequence can also be identified by using binding ligands which recognize a product of the selectable gene, e.g., an antibody can be used to identify a polypeptide product coded for by the selectable gene, an appropriate ligand can be used to identify expression of a receptor polypeptide coded for by the selectable gene, or by assaying for expression of an enzyme coded for by the selectable gene. Preferably, the selectable marker gene encodes a polypeptide that does not naturally occur in the mammal.

The selectable marker gene can be operably linked to its own promoter or to another promoter from any source that will be active or can easily be activated in the cell into which it is inserted. However, the selectable marker gene need not have its own promoter attached, as it may be transcribed using the promoter of the gene into which it is inserted. The selectable marker gene can comprise one or more sequences to drive and/or assist in its expression, including, e.g., ribosome-recognition sequences, enhancer sequences, sequences that confer stability to the polypeptide or RNA, and/or a polyA sequence attached to its 3' end to terminate transcription of the gene.

A positive selectable marker facilitates selection for recombinants in which the positive selectable marker has integrated into the target nucleic acid by homologous recombination. A gene targeting vector in accordance with the present invention can also further comprise a second selection characteristic coded for by a second selectable gene to further assist in the selection of correctly targeted recombinants. A negative selection marker permits selection against cells in which only non-homologous recombination has occurred. In one preferred embodiment, the second selectable marker gene confers a negative selection characteristic upon a cell in which it has been introduced. Such negative selection characteristics can be arranged in the targeting vector in such a way that it can be utilized to discriminate between random integration events and homologous recombination. By the term negative selection, it is meant a selection characteristic which, when acquired by the cell, results in its loss of viability (i.e., it is lethal to the cell). A nucleoside analog, gancyclovir, which is preferentially toxic to cells expressing HSV tk (herpes simplex virus thymidine kinase), can be used as a negative selection agent, as it selects for cells which do not have an integrated HSV tk selectable marker. FIAU (1,2-deoxy-2-fluoro-α-d-arabinofuransyl-5-iodouracil) can also be used as a selection agents to select for cells lacking HSV tk. Other negative selectable markers can be used analogously. Examples of negative selection characteristics and a corresponding thymidine kinase (HSV tk) and acyclovir, gancyclovir, or FIAU; Hprt and 6-thioguanine or 6-thioxanthine; diphtheria toxin; ricin toxin; cytosine deaminase and 5-fluorocytosine.

The negative selectable marker is typically arranged on the gene targeting vector 5' or 3' to the recombinogenic homology regions so that double-crossover replacement recombination of the homology regions transfers the positive selectable marker to a predefined location on the target nucleic acid but does not transfer the negative selectable marker. For example, a tk cassette can be located at the 3' end of a murine hepsin gene, about 150 base pairs from the 3' stop codon. More than one negative selectable marker can also be utilized in a targeting vector. The positioning of, for example, two negative selection vectors at the 5' and 3' ends of a targeting vector further enhances selection against target cells which have randomly integrated the vector. Random integration sometimes results in the rearrangement of the vector, resulting in excision of all or part of the negative selectable marker prior to random integration. When this occurs, negative selection cannot be used to eliminate those cells which have incorporated the targeting vector but by random integration rather than homologous recombination. The use of more than one negative selectable marker substantially enhances the likelihood that random integration will result in the insertion of at least one of the negative selectable markers. For such purposes, the negative selectable markers can be the same or different.

The use of a positive-negative selection scheme reduces the background of cells having incorrectly integrated targeted construct sequences. Positive-negative selection typically involves the use of two active selectable markers: (1) a positive selectable marker (e.g., neo) that can be stably expressed following random integration or homologous targeting, and (2) a negative selectable marker (e.g., tk) that can only be stably expressed following random integration. By combining both positive and negative selection, host cells having the correctly targeted homologous recombination event can be efficiently obtained. Positive-negative selection schemes are described, e.g., in U.S. Pat. No. 5,464,764; WO 94/06908. It is recognized, however, that one or more negative selectable markers are not required to carry out the present invention, e.g., produce a transgenic animal in which a serine protease gene is functionally inactivated or disrupted.

A recombinant nucleic acid molecule according to the present invention can also comprise all or part of a vector. A vector is, e.g., a nucleic acid molecule which can replicate autonomously in a host cell, e.g., containing an origin of replication. Vectors can be useful to perform manipulations, to propagate, and/or obtain large quantities of the recombinant molecule in a desired host. A skilled worker can select a vector depending on the purpose desired, e.g., to propagate the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR540, pRIT5 (Pharmacia). Eukaryotic: PWLNEO, pSV2CAT, pOG44, pXT1, pSG (Stratagene), pSVK3, PBPV, PMSG, pSVL (Pharmacia). However, any other vector, e.g., plasmids, viruses, or parts thereof, may be used as long as they are replicable and viable in the desired host. The vector can also comprise sequences which enable it to replicate in the host whose genome is to be modified. The use of such vector can expand the interaction period during which recombination can occur, increasing the targeting efficiency. An example of a gene targeting vector that can be used in accordance with the present invention is described in *Molecular Biology*, ed. by F. M. Ausubel et al., Unit 9.16, FIG. 9.16.1 (pNTK).

In accordance with an aspect of the present invention, the function of a serine protease gene, such as a hepsin gene, is disrupted or knocked out by the insertion of an exogenous or heterologous sequence into it, interrupting its function. For example, the exogenous or heterologous sequence can be inserted into a region of the hepsin gene before its first start codon. The nucleotide sequence coding for a selectable characteristic can be inserted into the hepsin gene in such a manner by homologous recombination so that it is operably linked to the endogenous promoter of the hepsin gene. Upon integration of the selectable marker gene into the desired predefined position of the hepsin gene, expression of the selectable characteristic is driven by the endogenous hepsin gene promoter, permitting its detection into those cells into which it has integrated.

The selectable marker gene can also be integrated at positions downstream of 3' to the first start codon of the hepsin gene. The hepsin gene can be integrated out-of-reading frame or in-reading frame with the hepsin polypeptide so that a fusion polypeptide is made, where the fusion polypeptide is less active than the normal product. By detecting only those cells which express the characteristic, cells can be selected which contain the integrated sequence at the desired location. A convenient way of carrying out such selection is using antibiotic resistance. In the examples below, neomycin resistance is utilized as the selectable characteristic. Cells grown in the presence of a toxic concentration of neomycin will normally die. Acquisition of the neomycin resistance gene by homologous recombination rescues cells from the lethal effect, thereby facilitating their selection.

The serine protease gene is knocked out or functionally interrupted by the integration event. The insertion of the selectable gene ahead of the hepsin coding sequence effectively isolates it from a promoter sequence, disabling its expression. If the selectable gene contains a transcription terminator, then transcription of the gene using the hepsin promoter will terminate immediately after it and will rarely result in the transcription of the hepsin coding sequence. The serine protease gene can also be knocked out by a deletion without a replacement, such as a site-directed deletion of a part of the gene. Deleted regions can be coding regions of regulating regions of the gene.

A hepsin gene can be modified at any desired position. It can be modified so that a truncated hepsin polypeptide is produced having one or more activities of the complete hepsin polypeptide. As already discussed, such a modified gene is a functionally disrupted gene. In the examples below, exons 5–8 of a murine hepsin gene are replaced by a neomycin resistance. Expression of the modified gene could result in a truncated polypeptide comprising exons 1–4 of hepsin. This polypeptide would comprise a transmembrane domain from amino acids 18–44; See, Leytus et al., Biochemistry, 27:1067–1074 (1988), but lack the catalytic domains and therefore would be functionally inactive. See Background for a description of hepsin activity. It is believed that such a truncated polypeptide would not be produced at all. The truncated mRNA would lack its 3' end which normally confers stability to the message. Consequently, the resultant mRNA would be unstable and therefore rarely, if at all, available for translation. Such truncated mRNA was not detected in RNA blots. The hepsin gene can be functionally interrupted so that a resultant product lacks the transmembrane domain completely or partially and/or comprises all or part of the catalytic domains, etc., as desired, and therefore lacks all or part of its activity, especially its enzymatic activity.

If desired, the insertion(s) can be removed from the recombinant gene. In the example, a neomycin cassette replaced exons of the mouse hepsin gene to functionally inactivate it. The neomycin cassette can be subsequently removed from the hepsin gene, e.g., using a recombinase system. The Cre-lox site specific recombination system is especially useful for removing sequences from a recombinant gene. To utilize the Cre-lox system, recombinase recognition sites are integrated into the chromosome along with the selectable gene to facilitate its removal at a subsequent time. For guidance on recombinase excision systems, see, e.g., U.S. Pat. Nos. 5,626,159, 5,527,695, and 5,434,066. See also, Orban, P.C., et al., "Tissue-and Site-Specific DNA Recombination in Transgenic Mice", Proc. Natl. Acad. Sci. USA, 89:6861–6865 (1992); O'Gorman, S., et al., "Recombinase-Mediated Gene Activation and Site-Specific Integration in Mammalian Cells", Science, 251:1351–1355 (1991); Sauer, B., et al., "Cre-stimulated recombination at loxP-Containing DNA sequences placed into the mammalian genome", Nucleic Acids Research, 17(1):147–161 (1989).

In the example, after excision of the neo gene, the splicing machinery could bypass the remaining part of exon 9, connecting the 3' end of exon 8 to the 5' end of exon 13. Thus, even if a correct reading frame were restored, the encoded protein still would lack the active enzymatic site.

A nucleic acid comprising a nucleotide sequence coding without interruption means that the nucleotide sequence contains an amino acid coding sequence for a polypeptide, with no non-coding nucleotides interrupting or intervening in the coding sequence, e.g., absent intron(s) or the noncoding sequence, as in a cDNA.

The present invention also relates to an isolated mouse hepsin or biologically-active fragments thereof. The term "isolated" means that the material is in a form in which it is not found in its original environment, e.g., it is more concentrated, more purified, or separated from components, etc. The fragments are preferably biologically-active. By biologically-active, it is meant that the polypeptide fragment possesses an activity in a living system or with components of a living system. Biological-activities of hepsin or a fragment thereof include: immunogenic activity, targeting to the cell membrane, insertion in the cell membrane (e.g., where the fragment comprises the N-terminal transmembrane domain), cell signaling (e.g., in morphogenesis or development, e.g., of bone or cartilage), activation of blood coagulation factor VII, tumor-related hypercoagulability, hydrolysis of synthetic substrates, and/or growth factor activity. For these and other hepsin activities, see also the Background section above and the references discussed therein. A hepsin fragment can contain one or more activities. Immunogenic activity means that the polypeptide binds to hepsin specific antibodies or is capable of eliciting an immune response specific for a hepsin. A hepsin polypeptide, or corresponding nucleic acid coding for it, means a polypeptide which can be isolated from a natural source. It therefore includes naturally-occurring normal and mutant alleles. Natural sources include, e.g., living cells obtained from tissues and whole organisms, and cultured cell lines. Fragments can be prepared routinely, e.g., by recombinant means or by proteolytic cleavage of isolated polypeptides, and then assayed for a desired activity.

Another aspect of the present invention relates to host cells comprising a recombinant nucleic acid of the invention. A cell into which a nucleic acid is introduced is a transformed cell. Host cells include, mammalian cells, e.g., murine Ltk-, murine embryonic stem cells, COS-7, CHO, HeLa, insect cells, such as Sf9 and Drosophila, bacteria, such as *E. coli*, Streptococcus, bacillus, yeast, fungal cells, plants, embryonic stem cells (e.g., mammalian, such as mouse or human), neuronal cells (primary or immortalized), e.g., NT-2, NT-2N, PC-12, SY-5Y, neuroblastoma. See, also *Methods in Enzymology*, Volume 185, ed., D. V. Goeddel. A nucleic acid can be introduced into the cell by any effective method including, e.g., calcium phosphate precipitation, electroporation, injection, pressure, DEAE-Dextran mediated transfection, fusion with liposomes, and viral transfection. When the recombinant nucleic acid is present in a mouse cell, it is preferably integrated by homologous recombination into the mouse cell gene locus.

A transformed cell can contain a recombinant gene integrated into its chromosome at the targeted gene locus. A targeting vector which comprises sequences effective for homologous recombination at a particular gene locus, when introduced into a cell under appropriate conditions, will recombine with the homologous sequences at the gene locus, introducing a desired selectable gene into it. When recombination occurs such that insertion results, the nucleic acid is integrated into the gene locus. The gene locus can be the chromosomal locus which is characteristic of the species, or it can be a different locus, e.g., translocated to a different chromosomal position, on a supernumerary chromosome, on an engineered "chromosome," etc.

As discussed below, the present invention also relates to transgenic animals containing one or more modified serine protease genes. The transgenic animals produced in accordance with the present invention can be used as a source to establish primary or established, e.g., immortalized, cell lines according to various methods as the skilled worker would know. Since the animals (either homozygotes or heterozygotes) contain a modified serine protease gene, e.g., hepsin, the corresponding cell lines would be expected to have the same genotype. The cell lines can be derived from any desired tissue or cell-type, including, e.g., liver, epithelia, neuron, fibroblast, mammary, lung, kidney, pancreas, stomach, thyroid, prostate, osteoblasts, osteoclasts, osteocytes, osteoprogenitor cells, muscle (e.g., smooth), etc.

Cell lines produced in accordance with the present invention are useful for a variety of purposes. In one aspect of the invention, it is desirable to create panels of cell lines which differ in the expression of one or more genes. For example, the present invention describes and enables the production of cell lines which lack a serine protease gene, such as the hepsin gene. A hepsin-functionally-disrupted cell line differs from the parental (i.e., starting) cell line by the expression of the hepsin gene. The availability of such pairs of cell lines, i.e., plus or minus for hepsin expression (or any other desired gene or genes), is useful to distinguish the effects of hepsin from those of other genes products, such as other serine proteases. Hepatocyte lines, such as HepG2 or PLC/PRF/5 cells, express a variety of different proteases, including, thrombin, factors Xa, IXa, and VIIa, protein C and hepsin. A cell line functionally-disrupted in one or more desired proteases (e.g., hepsin), in combination with the parental cell line intact for the desired protease(s), can be employed to specifically distinguish its activity (e.g., hepsin) from all other proteases. Such genetic dissection can be used to develop, e.g., drugs and therapeutics which target a specific gene product, e.g., hepsin, thrombin, factors Xa, IX, and VIIa, and protein C, the latter proteases which play roles in cardiovascular and blood diseases. For example, to prevent clots, it is desirable to develop reagents which inhibit a specific protease in a cellular system. Inhibition of other proteases involved in other biological processes is undesirable since it can lead to secondary and unwanted side effects. A protease inhibition assay using cells or proteases obtained from, e.g., hepatocytes, would be unable to distinguish between the different proteases (i.e., enzymatic activities) expressed by the same cells. By using cell lines in which one or more proteases are genetically knocked out, the effects of such inhibitors can be identified more specifically (e.g., an inhibitor which inhibits protease activity equally in the hepsin-functionally disrupted cell line and its parent would be considered to be a non-hepsin-specific protease inhibitor). For hepsin, such pairs (or more) of cell lines are useful in identifying agents to treat pathological conditions in which hepsin activity plays a role, e.g., ischemic heart disease, cardiovascular deficiency, tumor-related hypercoagulation, intravascular thrombosis, cell and growth control, etc. Additionally, since hepsin is a cell-surface protein, hepsin-functionally disrupted cell lines can be combined with hepsin-complete cell lines, etc., to study the interactions and identify, e.g., the cell surface receptor for the hepsin gene product. These plus/minus screening methods can be adapted to any desired gene(s) or gene product(s).

Accordingly, another aspect of the invention relates to a method of identifying an agent which modulates an activity of a mammalian gene product, e.g., a serine protease such as hepsin. By the phrase "an agent which modulates the activity," it is meant that the agent affects the activity. The activity can be affected by reducing it, eliminating it, activating it, increasing it, changing its specificity, etc. The agent can be an agonist, an antagonist, or a partial agonist or antagonist. The agent can be administered to a cell, an organ, a tissue, a whole organism, etc. Administration can be accomplished in various ways, e.g., by addition of it directly to a medium bathing or perfusing the cells, by encapsulating it in a liposome or a cyclodextran, etc., by complexing it to another agent such as a chelating agent, DEAE, etc., by expressing it from a cell, by a virus, by injection, by inhalation, etc. Generally, the method comprises: (1) administering to a first cell in which expression of at least one copy of a target gene is functionally disrupted, (2) administering said agent to a second cell which contains at least one more copy of the first cell target gene whose expression is complete, and (3) measuring the amount of activity of the target gene in the first and second cell. The difference in the amount of activity can be used to determine whether the agent is selective for the target gene whose function is disrupted. By the phrase "expression is complete," it is meant, e.g., that the expression of the gene is wild-type or that the gene's product contains 1 or more desired activities.

Gene functionally-disrupted cell lines can also be utilized to produce transgenic, either chimeric, heterozygous, or homozygous, animals, e.g., non-human mammals. Such transgenic animals are useful as models to study the physiological role of a desired gene and to identify agents which specifically target the desired gene or a biological pathway in which it acts. Thus, an aspect of the invention is method of administering to a mammal functionally-disrupted for a serine protease, e.g., hepsin, an amount of an agent effective to restore the serine protease, e.g., hepsin, function. Such agent can be, e.g., the gene, itself, e.g., as in administering the hepsin gene, an agonist, or an agent which acts upstream of the serine protease. Such animals are also useful for identifying the specific function and/or role of the knocked out gene. Hepsin-related disorders include ischemic heart disease, cardiovascular deficiency, tumor-related hypercoagulation, intravascular thrombosis, cell and growth control (e.g., cancer, hyper-or hypo-proliferative diseases, etc.), bone diseases. The use of animal models functionally disrupted for the hepsin gene is useful for identifying agents useful in treating such disorders, developing diagnostic agents and criteria for these disorders, etc. For example, hepsin-functionally-disrupted mammals, such as mice, are useful to identify blood plasma protein levels of hepsin and changes related to hepsin levels, for diagnostic and treatment purposes. A transgenic animal and a recombinant nucleic acid molecule according to the present invention is useful as described in U.S. Pat. Nos. 5,557,032, 5,532,158, 5,304,489, 5,221,778, 5,175,385, 5,175,384, 5,175,383, 5,087,571, 5,082,779, 4,736,866, 4,873,191, and other transgenic animal patents.

The invention also relates to the treatment of bone and skeletal disorders (e.g., osteoporosis, Paget's disease, osteitis deformans, etc.), especially those associated with elevated bone alkaline phosphase ("AP") levels. For example, a transgenic homozygous hepsin "knock-out" animal in accordance with the present invention can be used as an animal model for a bone disease. These animals exhibit elevated levels of serum alkaline phosphatase ("AP"), especially AP of bone origin. See, e.g., FIGS. 3 and 4. By the phrase "elevated levels of serum AP", it is meant, e.g., an amount of circulating AP which is increased above the normal range established for animals of the same genetic background. The increase in AP is statistically significant, e.g., within 95%, preferably 99%, confidence levels as measured by a t-test. See, e.g., FIG. 3. The amount of elevation can be, e.g., 5%, 10%, 20%, 50%, etc., above normal.

In one embodiment, agents can be administered to transgenic animals to determine their effect on the treatment and/or prevention of bone disease. The effect can be monitored in various ways, including by direct inspection, e.g., bone X-ray, or indirectly by measuring circulating AP levels. The modulation in the AP level indicates an effect on the bone disease. The agents can be of any composition desired (polypeptide, nucleic acid, organic, inorganic, etc.). An agent can be combined with another agent known to effect the bone disease, e.g., calcitonin, bisphosphonates, gallium nitrate, etc.

A knockout mouse in accordance with the present invention can also be used as a diagnostic tool to develop sensitive assays for alkaline phosphatase. Alkaline phosphatase is routinely tested and utilized as a clinical marker for a variety of diseases, including cancer, bone diseases. Thus, trangenic animals having elevated AP levels can be used to design and develop sensitive assays for AP detection. For example, the present invention can be utilized to identify agents which modulate alkaline phosphatase activity, e.g., increase its activity and therefore enhance its detection.

The functionally-disrupted hepsin-gene can also be employed as a marker to identify mice which are otherwise undistinguishable. For example, if one desires to know the source of an animal (e.g., a mouse in a mixed cage of animals), genotype analysis can be performed (e.g., on blood, tail tissue, etc.) to determine whether any contain the hepsin-disrupted gene locus, thus identifying the animal's origin.

The present invention also relates to a non-human transgenic animal, preferably a mammal, more preferably a mouse, which comprises a serine protease gene, preferably a hepsin gene, which has been engineered employing a recombinant nucleic acid according to the present invention. Generally, a transformed host cell, preferably a totipotent cell, whose endogenous gene has been modified using a recombinant nucleic acid as described above is employed as a starting material for a transgenic embryo. The preferred methodology for constructing such a transgenic embryo involves transformed embryonic stem (ES) cells employing a targeting vector comprising a recombinant nucleic acid according to the invention. A particular gene locus, e.g., hepsin, is modified by targeted homologous recombination in cultured ES cells employing a targeting vector comprising a recombinant nucleic acid according to the invention. The ES cells are cultured under conditions effective for homologous recombination. Effective conditions include any culture conditions which are suitable for achieving homologous recombination with the host cell chromosome, including effective temperatures, pH, medias, additives to the media in which the host cell is cultured (e.g., for selection, such as G418 and/or FIAU), cell densities, amounts of DNA, culture dishes, etc. Cells having integrated the targeting vector are selected by the appropriate marker gene present in the vector. After homologous recombination has been accomplished, the cells contain a chromosome having a recombinant gene. In a preferred embodiment, this recombinant gene contains a positive selectable marker gene fused to endogenous hepsin gene sequences.

The transformed or genetically modified ES cells can be used to generate transgenic non-human mammals, e.g., mice, by injection into blastocysts and allowing the chimeric blastocysts to mature, following transfer into a pseudopregnant mother. See, e.g., *Teratomacarcinoma and Embryonic Stem Cells: A Practical Approach*, E. J. Robertson, ed., IRL Press. Various stem cells can be used, as known in the art, e.g., AB-1, HM-1 D3, CC1.2, E-14T62a, or RW4. Offpsring born to foster mothers may be screened initially for mosaic coat color where a coat color selection strategy has been employed. Alternatively, DNA from tail tissue of the offpsring can be used to screen for the presence of the DNA targeting vector. Offpsring that appear to be mosaics are then crossed to each other, if it believed they carry the modified gene in their germ line, in order to generate homozygotes for the modified gene. See, e.g, U.S. Pat. No. 5,557,032; U.S. Pat. No. 5,532,158.

In addition to the ES cell methods described here, transgenic animals can be created by other methods, e.g., by pronuclear injection of recombinant genes into pronuclei of one-cell embryos, incorporating an artificial yeast chromosome into embryonic stem cells, gene targeting methods, embryonic stem cell methodology. See, e.g., U.S. Pat. Nos. 4,736,866; 4,873,191; 4,873,316; 5,082,779; 5,304,489; 5,174,986; 5,175,384; 5,175,385; 5,221,778; Gordon et al., *Proc. Natl. Acad. Sci.*, 77:7380–7384 (1980); Palmiter et al., *Cell*, 41:343–345 (1985); Palmiter et al., *Ann. Rev. Genet.*, 20:465–499 (1986); Askew et al., *Mol. Cell. Bio.*, 13:4115–4124 (1993); Games et al. *Nature*, 373:523–527 (1995); Valancius and Smithies, *Mol. Cell. Bio.*, 11:1402–1408 (1991); Stacey et al., *Mol. Cell. Bio.*, 14:1009–1016 (1994); Hasty et al., *Nature*, 350:243–246 (1995); Rubinstein et al., *Nucl. Acid Res.*, 21:2613–2617 (1993).

As discussed, the invention relates to a transgenic mammal, such as a mouse, comprising cells which contain at least one functionally disrupted recombinant hepsin gene (e.g., heterozygous or homozygous) at a chromosomal hepsin gene locus. The cells can be created in accordance with the example below by inserting an exogenous nucleotide sequence into the hepsin gene. However, other methods can be used to create a functionally interrupted gene. For example, a termination codon can be inserted into the hepsin gene, using, e.g., a replacement type vector as described in Rubinstein et al., Nucleic Acid Research, 21: 2613–2617, 1993 or a tag-and-exchange strategy as described in Askew et al., Mol. Cell. Bio., 13: 4115–4124, 1993, etc. Functional interruption of a hepsin gene can also be achieved classically by mutagenesis, such as chemical or radiation mutagenesis.

A recombinant nucleic acid molecule according to the present invention can be introduced into any non-human mammal, including a mouse (Hogan et al., *Manipulating the Mouse Embryo: A Laboratory Manual*, Cold Spring Harbor Laboratory, Cold Spring Harbor, New York, 1986), pig (Hammer et al., *Nature*, 315:343–345, 1985), sheep (Hammer et al., *Nature*, 315:343–345, 1985), cattle, rat, or primate. See also, e.g., Church, Trends in Biotech. 5:13–19, 1987; Clark et al., *Trends in Biotech.* 5:20–24, 1987; and DePamphilis et al., *BioTechniques*, 6:662–680, 1988. In the examples below, a murine hepsin gene is modified by homologous recombination utilizing a gene targeting vector comprising regions of the murine hepsin gene. To carry out genetic modification of another mammalian hepsin gene, e.g., a rat or a primate, it may be desirable to obtain analogous regions of the target hepsin gene. A hepsin gene from another species, using a murine or human hepsin gene, can be accomplished by various methods known in the art, e.g., PCR using a mixture of oligonucleotides based on a consensus sequence or serine proteases and/or hepsins (e.g., Leytus et al., *Biochemistry*, 27: 1067–1074, 1988), nucleic acid hybridization using oligonucleotides, cDNA, etc., at a desired stringency (e.g., Sambrook et al., *Molecular Cloning*, 1989, Chapter 11).

A transgenic animal according to the present invention can comprise one or more genes which have been modified by genetic engineering. For example, a transgenic animal comprising a hepsin gene which has been modified by targeted homologous recombination in accordance with the present invention can comprise other mutations, including modifications at other gene loci and/or transgenes. Modifications to these gene loci and/or introduction of transgenes can be accomplished in accordance with the methods of the present invention, or other methods as the skilled worker would know. For instance, double-mutants can be made by conventional breeding, i.e., crossing animals and selecting for a desired phenotype and/or genotype. In one embodiment of the invention, a transgenic animal can be constructed having at least one gene defective in hepsin (e.g., a knock-out) and one or more defective genes coding for a product utilized in the blood coagulation pathway, e.g., factor VII or factor IX. In a preferred embodiment, the latter genes are null or functionally-disrupted. Such an animal can be homozygous or heterozygous for the desired loci, or a combination thereof.

The present invention also relates to a murine hepsin specific amino acid sequence selected from the sequence of amino acid 1 to 417 as set forth in FIG. 2. A murine hepsin specific amino acid sequence means a defined amino acid sequence which is found in the recited hepsin sequence but not in another amino acid sequence, especially not another hepsin sequence. A specific amino acid sequence can be found routinely, e.g., by searching a gene/protein database using the BLAST set of computer programs. A murine hepsin cDNA can be useful, e.g., as a probe to obtain murine genomic DNA or to produce peptides as antigens to generate an immune response specific for murine hepsin. Antibodies obtained by such immunization can be used as a specific probe for the murine hepsin for diagnostic or research purposes. Such peptides can also be used to inhibit a hepsin activity in cells or cell-free systems.

A murine hepsin polypeptide, fragment, or murine hepsin polypeptide can also comprise various modifications, where such modifications include glycosylation, covalent modifications (e.g., of an R-group of an amino acid), amino acid substitution, amino acid deletion, or amino acid addition. Modifications to the polypeptide can be accomplished according to various methods, including recombinant, synthetic, chemical, etc.

A polypeptide according to the present invention can be produced in an expression system, e.g., in vivo, in vitro, cell-free, recombinant, cell fusion, etc., according to the present invention. Modifications to the polypeptide imparted by such system include, glycosylation, amino acid substitution (e.g., by differing codon usage), polypeptide processing such as digestion, cleavage, endopeptidase or exopeptidase activity, attachment of chemical moieties, including lipids, phosphates, etc. For example, some cell lines can remove the terminal methionine from an expressed polypeptide.

A polypeptide according to the present invention can be recovered from natural sources, transformed host cells (culture medium or cells) according to the usual methods, including, ammonium sulfate or ethanol precipitation, acid extraction, anion or cation exchange chromatography, phosphocellulose chromatography, hydrophobic interaction chromatography, hydroxyapatite chromatography and lectin chromatography. Protein refolding steps can be used, as necessary, in completing the configuration of the mature protein. Finally, high performance liquid chromatography (HPLC) can be employed for final purification steps.

For other aspects of the nucleic acids, polypeptides, antibodies, etc., reference is made to standard textbooks of molecular biology, protein science, and immunology. See, e.g., Davis et al. (1986), *Basic Methods in Molecular Biology*, Elsevir Sciences Publishing, Inc., New York; Hames et al. (1985), *Nucleic Acid Hybridization*, IL Press, *Molecular Cloning*, Sambrook et al.; *Current Protocols in Molecular Biology*, Edited by F. M. Ausubel et al., John Wiley & Sons, Inc; *Current Protocols in Human Genetics*, Edited by Nicholas C. Dracopoli et al., John Wiley & Sons, Inc.; *Current Protocols in Protein Science*; Edited by John E. Coligan et al., John Wiley & Sons, Inc.; *Current Protocols in Immunology*; Edited by John E. Coligan et al., John Wiley & Sons, Inc.

EXAMPLES

Cloning of Mouse Hepsin cDNA:

Mouse hepsin cDNA was cloned using a PCR-based strategy. Total RNA was isolated from mouse liver with a CsCl gradient ultracentrifugation method (Sambrook et al., *Molecular Cloning: A Laboratory Manual*, Cold Spring Harbor Laboratory Press, Cold Spring Harbor, N.Y., 1989). Single-stranded cDNAs were synthesized from 12 μg total RNA using avian myeloblastosis virus reverse transcriptase and an oligo(dT) primer (cDNA Cycle Kit, Invitrogen). The cDNAs were used as templates for PCR amplification (30 cycles of 1.5-min annealing at 55° C., 1.5-min extension at 72° C., and 1-min denaturation at 94° C.) with sense primer 5'-TTC GCC ATC TGC CAA GAC TG-3' (SEQ ID NO:3) and anti-sense primer 5'-GTG AGT CTT TAT GGC CTG GAA GAT-3' (SEQ ID NO:4). The sequences of primers are based the published sequence of human hepsin cDNA (Leytus et al., *Biochemistry* 27:1067–1074, 1988).

A 785-bp DNA fragment amplified from the PCR reaction was cloned into the plasmid vector pCR (Invitrogen). Sequencing of the DNA fragment showed that it shared >90% sequence identity with human hepsin cDNA. Additional clones were obtained by radiolabeling of the cDNA fragment with [$^{32}$P]dCTP and screening of mouse liver cDNA (Wetsel et al, *J. Biol. Chem.* 265:2435–2440, 1990) or genomic libraries (Stratagene) or by using oligocucleotides to screen 5' rapid amplification of cDNA ends (RACE) libraries (Clontech). A full-length mouse cDNA sequence is shown in FIG. 2. Mouse and human hepsin cDNAs share over 84% sequence identities.

Cloning of Mouse Genomic Gene:

To clone the mouse hepsin genomic gene, a partial murine cDNA was purified and radiolabeled with [$^{32}$P]dCTP using a random primer labeling kit (Amershan). The probe was used to screen a 129Sv mouse genomic library (Stratagene). Hybridization was performed with 2×10$^6$ cpm/ml radiolabeled probe, 40% formamide, 6×SSC, 5 × Denhardt's solution, 0.1% SDS and 100 μg/ml salman sperm DNA. One positive clone was identified after screening of 8×10$^4$ phage clones. Lambda phage DNA from this clone was purified using a phage preparation kit from Stratagene. The genomic DNA insert was isolated by restriction enzyme digestion and subsequently cloned into plasmid vector Bluescript (Stratagene).

The genomic structure of the mouse hepsin gene was determined by restriction enzyme digestion, hybridization with radiolabeled oligonucleotides, subcloning of DNA fragments and sequencing. As shown in FIG. 1, the mouse hepsin gene spans ~15 kb and contains at least 12 exons shown in black boxes. The three serine protease active site residues His (H), Asp (D) and Ser (S) are encoded by exons 7, 8 and 11, respectively. Selected restriction enzyme sites are indicated in FIG. 1 by the vertical lines.

Construction of the Targeting Vector:

To construct the targeting vector, exons 5–8 of the hepsin gene were deleted and replaced by a neo gene cassette that serves as a positive selection marker (FIG. 1) (Capecchi, *Science* 244: 1288–1292, 1989). The deletion abolished the potential hepsin activation cleavage site as well as the protease catalytic site His and Asp residues. At the 3' end of the vector, a herpes simplex virus thymidine kinase (tk) gene cassette was also included to serve as a negative selection marker (FIG. 1) (Capecchi, *Science* 244:1288–1292, 1989). The structure of the targeting vector was verified by restriction enzyme digestion and DNA sequencing. Large scale preparation of supercoiled plasmid DNA was performed using a CsCl gradient ultracentrifugation method (Sambrook et al, *Molecular Cloning: A Laboratory Manual*, Cold Spring Harbor Laboratory Press, Cold Spring Harbor, N.Y., 1989).

Disruption of the Hepsin Gene in Mouse Embryonic Stem Cells:

Pluripotent mouse embryonic stem (ES) cells (RW4) were purchased from Genome Systems (St. Louis). ES cells were cultured in 100-mm petri dishes containing a layer of primary mouse embryonic fibroblasts that were pretreated with 10 μg/ml mitomycin C (Joyner A, *Gene Targeting: A Practical Approach*, IRL Press, N.Y., 1993). ES cell culture medium consists of DMEM (Gibco), 15% fetal bovine serum (Hyclone), 2 mM L-glutamine, 1 mM sodium pyruvate, 0.1 mM non-essential amino acid, 20 mM Hepes, 11 μM 2-mercaptoethanol, 50 μg/ml penicillin-streptomycin, and 10$^3$ U/ml leukemia inhibitory factor (LIF) (Gibco).

The targeting vector was introduced into ES cells by electroporation using Electro Cell Manipulator (ECM 600, BTX Inc.) under conditions recommended by the manufacturer. A total of 1.5×10$^7$ ES cells was transfected with 30 μg of linearized vector DNA. Transfected ES cells were cultured in 100-mm petri dishes and selected in the presence of 250 μg/ml G418 (Gibco) and 2 μM ganciclovir (Syntex Laboratories, Inc.). Over 700 stable transfected cell lines from the selection were obtained. Genomic DNA from the cells was isolated and digested with restriction enzyme HindIII. Southern analysis was performed with a mouse hepsin genomic probe flanking the hepsin gene deletion and a neo gene probe.

Seven mutant ES cell lines were identified in which one copy of the endogenous hepsin gene was disrupted by homologous recombination. The disruption occurred only at the single locus and there was no additional neo gene insertion found in the genome. Karyotypic analysis (Chromosome Inc, St. Louis) showed that six cell lines had a normal male karyotype (40, XY). The predicted genomic structure in the mutant allele after homologous modification is shown in the lower panel of FIG. 1.

Generation of Chimeric Mice and Germline Transmission of the Mutant Allele:

To produce chimeric mice, four mutant ES cell lines were selected for blastocyst microinjection experiments that were performed by a commercial service, Stem Cell Gene Altered Mouse Core Service, University of Cincinnati (Cincinnati, OH.). Mouse blastocysts were derived from wild-type C57Bl/6J mice. About 10–15 hepsin mutant ES cells were injected into each blastocyst under a microscope. The blastocysts were further implanted into the uterus of pseudogregnant foster mothers. Implantation of 435 blastocysts yielded 36 chimeric offspring. Ninety percent of the animals have >50% coat color chimerism, an indication of significant ES cell contribution in the animals.

All chimeric mice were bred with NIH black swiss mice. Germline transmission was achieved with nine chimeric mice that were derived from injections of three independent cell lines. Breeding of these chimeric mice produced a total of 108 agouti pups.

Genomic DNA was obtained from mouse tail biopsy samples using Puregene DNA Isolation kit (Gentra Systems, NC). Genotypes of the agouti mice were determined by a PCR-based method. In the PCR reaction two sets of oligonucleotide primers were included: one set specific for the neo gene (sense primer: 5'-CAA GAT GGA TTG CAC GCA GG-3'(SEQ ID NO:5); anti-sense primer: 5'-GTA AAG CAC GAG GAA GCG G-3'(SEQ ID NO:6)) and another set specific for the hepsin gene (sense primer: 5'-ACG GCA CAT CGG GCT TCT TTT-3'(SEQ ID NO:7); antisense primer: 51-AAT GCG GTC CAC CGG CAG CTT CCT-3' (SEQ ID NO:8)). In each reaction, about 100 ng of genomic DNA was used as templates for the amplification (30 cycles of 1.5-min annealing at 59° C., 1.5-min extension at 72° C., and 1-min denaturation at 94° C.). The neo gene was identified in 49 agouti offspring, indicating germline transmission of the mutant hepsin allele. The results of PCR analysis were further confirmed by Southern analysis using the hepsin genomic probe.

Generation of Homozygous Hepsin-deficient Mice:

Male and female heterozygous hepsin-deficient mice were bred and over 400 offspring were produced. The genotype of these newborn mice was determined by the PCR analysis, as described the previous section. The PCR reaction allows us to determine genotypes of wild-type, heterozygous and homozygous mice.

Northern Analysis of Hepsin mRNA Expression:

Total RNA was extracted from frozen liver tissue using the UltraspecTM RNA kit (Biotecx Lab. Inc., Houston, Tex.). Samples (15 mg) were fractionated on denaturing agarose gels, transferred onto nitrocellulose membranes and hybridized with $^{32}$P-labeled mouse hepsin cDNA probes spanning the entire coding region. To determine mRNA expression of other liver specific genes, the blot was reprobed with a partial mouse prothrombin cDNA that was PCR-amplified based on the published sequence. Degen, S. J. F., Schaefer, L. A., Jamison, C. S., Grant, S. G. Fitzgibbon, J. J. Pai, J.-A., Chapman, V. M., & Elliott, R. W. (1990) *DNA & Cell Biol.*, 9, 487–498.

Hemostasis Assays and Blood Chemistry Analysis:

Blood samples were drawn from the inferior vena cava into one-tenth volume of 3.8% sodium citrate. Blood cell counts and hematocrit were analyzed using a hemostasis instrument (9210 CP Baker System). Clotting assays (aPTT and PT) were performed with platelet poor plasma using the MLA Electra 900C programmable coagulometer. In the tail bleeding assay, mice were anesthetized with pentobarbital (90 mg/kg). The tip of the mouse tail (1 mm in diameter) was cut. Tails were soaked immediately in 0.9% NaCl saline prewarmed at 37° C. and the time until bleeding stopped completely was recorded. For blood chemistry analysis, serum samples were prepared from clotted whole blood. Chemistry analysis was performed by Consolidated Veterinary Diagnostics, Inc., West Sacramento, Calif. Alkaline phosphatase isoenzymes were analyzed by a quantitative method described by Koffmann et al. Koffmann, W. E., Everds, N., Pignatello, M., & Solter, P. F. (1994) *Toxicol., Pathol.* 22, 633–638.

LPS-induced Septic Shock and Thromboplastin-induced DIC:

In the lipopolysaccharide (LPS)-induced septic shock model, mice (13–14 weeks old) were injected intraperitoneally with 40 mg/kg of LPS from *E. coli* serotype 0111:B4 (Calbiochem). The mice were monitored for signs of endotoxemia and lethality 4 times a day for the first 3 days and periodically thereafter. In the thromboplastin-induced disseminated intravascular coagulation (DIC) model, anesthetised mice were injected intravenously with human placental thromboplastin (Behring, Marburg, Germany). The linear range of the thromboplastin dose was determined experimentally. The time in minutes was recorded between the injection of thromboplastin and acute death as measured by cessation of breathing or heart beating.

Histological Analysis:

Mice were sacrificed under $CO_2$ narcosis and tissues were fixed by perfusion through the heart with an aldehyde fixative consisting of 4% (w/v) paraformaldehyde, 3% (w/v) sucrose, in 0.1 M phosphate buffer, pH 7.3. Tissues were dehydrated in graded ethanol solutions and embedded in paraffin blocks. Tissue sections were cut at 5 μm thickness, stained with hematoxylin and eosin (H & E), and examined by light microscopy.

Disruption of the Hepsin Gene in ES Cells and Generation of Chimeric Mice:

An 18-kb DNA fragment that contained the mouse hepsin gene was isolated from a 129Sv genomic library. The hepsin gene contains at least 12 exons (FIG. 1). The serine protease active site residues, His, Asp, and Ser are encoded by exons 7, 8, and 11, respectively. A replacement targeting vector was constructed by deleting the Kpn I/Bam HI fragment containing exons 5–8 that code for the conserved activation site and most of the catalytic domain (FIG. 1). Over 700 stable ES cell clones transfected with the targeting vector were analyzed by Southern blotting. Seven ES clones were identified in which one copy of the endogenous hepsin gene was disrupted by homologous recombination. Four mutant ES clones were microinjected into blastocysts from C57BL/6J mice to generate chimeric mice. Germline transmission was achieved with nine chimeric mice derived from three independent cell lines. The results of phenotypical analysis were obtained from mice derived from all these three ES cell lines.

Viability, Growth and Fertility of Homozygous Hepsin-/- Mice:

Breeding of hepsin+/- mice produced over 500 offspring. Genotypes of F2 progeny were determined by PCR analysis and the results were confirmed by Southern blotting in randomly selected samples. Wild-type, hepsin+/- and hepsin-/- mice represented 24.3%, 50.0% and 25.7% of progeny, respectively. The observed Mendelian pattern of inheritance indicates that homozygous hepsin-deficiency is compatible with normal embryonic development. Male to female ratio was ≈1:1 in wild-type, hepsin+/- and hepsin-/- mice. The absense of hepsin mRNA expression in liver samples from hepsin-/- mice was demonstrated by Northern analysis using cDNA probes spanning the entire coding region. As a control, the expression of prothrombin mRNA in the liver from hepsin-/- mice was not significantly affected.

When followed to 9 months, hepsin-/- mice appeared to develop normally and exhibited similar body weight gain as wild-type and hepsin+/- litter mates. No obvious physical abnormalities were observed in hepsin-/- mice. In hematologic examinations, values for red blood cell, white blood cell and platelet counts, hematocrit and hemoglobin were similar in hepsin-/- mice and wild-type controls. Both male and female hepsin-/- mice were fertile and produced viable offspring.

Tail Bleeding and Plasma Clotting Assays in Hepsin-/- mice:

To evaluate the physiological importance of hepsin function in blood coagulation, tail bleeding time and plasma clotting times (aPTT and PT) were determined in hepsin-/- mice. The mouse tail bleeding time measures both platelet and blood clotting activities, whereas aPTT and PT assays measure the function of the intrinsic and extrinsic blood coagulation pathways, respectively. As shown in Table 1, no prolongation in time was detected in hepsin-/- mice in these three assays, indicating that hepsin deficiency did not adversely affect hemostasis. These results are consistent with the observation that no spontaneous bleedings occurred in hepsin-/- mice.

Thromboplastin-induced DIC and LPS-induced Septic Shock Models:

To examine the potential function of hepsin under pathological conditions, hepsin-/- mice were challenged in DIC and septic shock models. In the DIC model, thromboplastin was injected intravenously. The times at which breathing or heart beating stopped were similar in both hepsin-/- mice and wild-type controls (Table 1), indicating that the tissue factor-dependent coagulation pathway was not altered in hepsin-/- mice. This was supported by the results from a septic shock model, in which survival rates of hepsin-/- and wild-type mice after injection of a high dose of LPS were not significantly different.

Figure 3A:
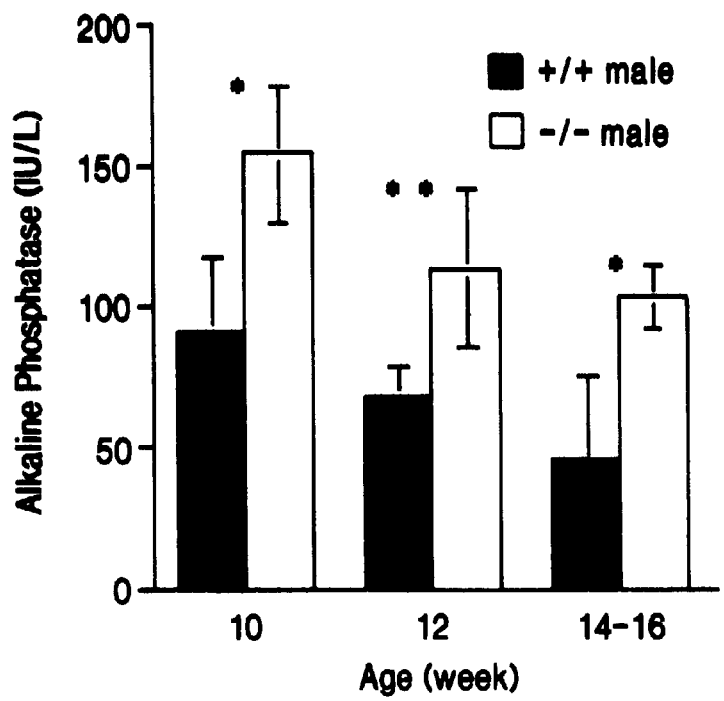
FIG. 3. Serum alkaline phosphatase levels in hepsin-deficient and control mice. Serum samples were prepared from male (upper panel) and female (lower panel) hepsin–/– mice and wild-type litter mates at 10, 12 and 14–16 weeks of age. The number of mice in each group is 4 to 5. Total serum alkaline phosphatase activity was measured by hydrolysis of p-nitrophenylphosphate at pH 9.2, McComb, R. B., Bowers, Jr., G. N., Posen, S. in Alkaline Phosphatase, Plesum Press, New York, 1979. Data are presented as mean±SD. Statistical differences between hepsin–/– mice (open bars) and wild-type litter mates (filled bars) are indicated by asterisks, $*P<0.05$, $**P<0.01$ by Student's t test.
Figure 3B:
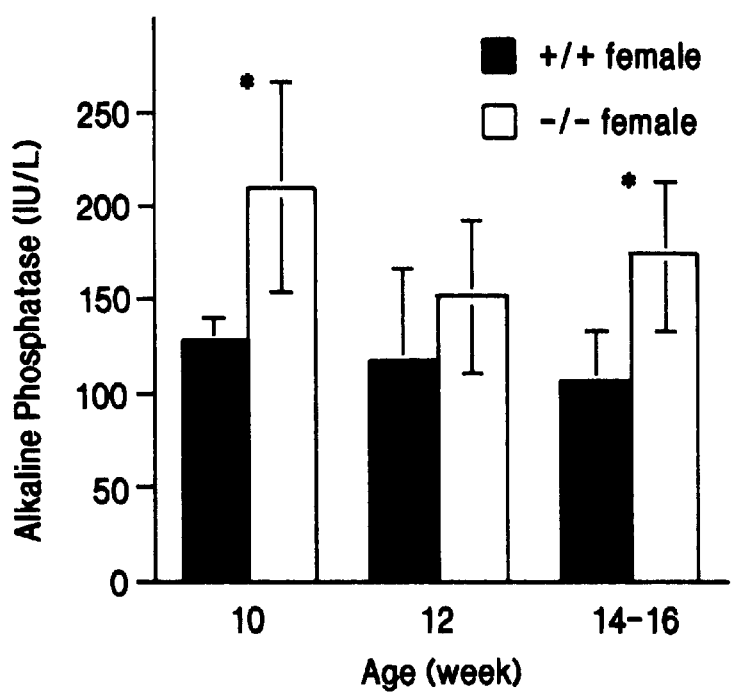
Figure 4:
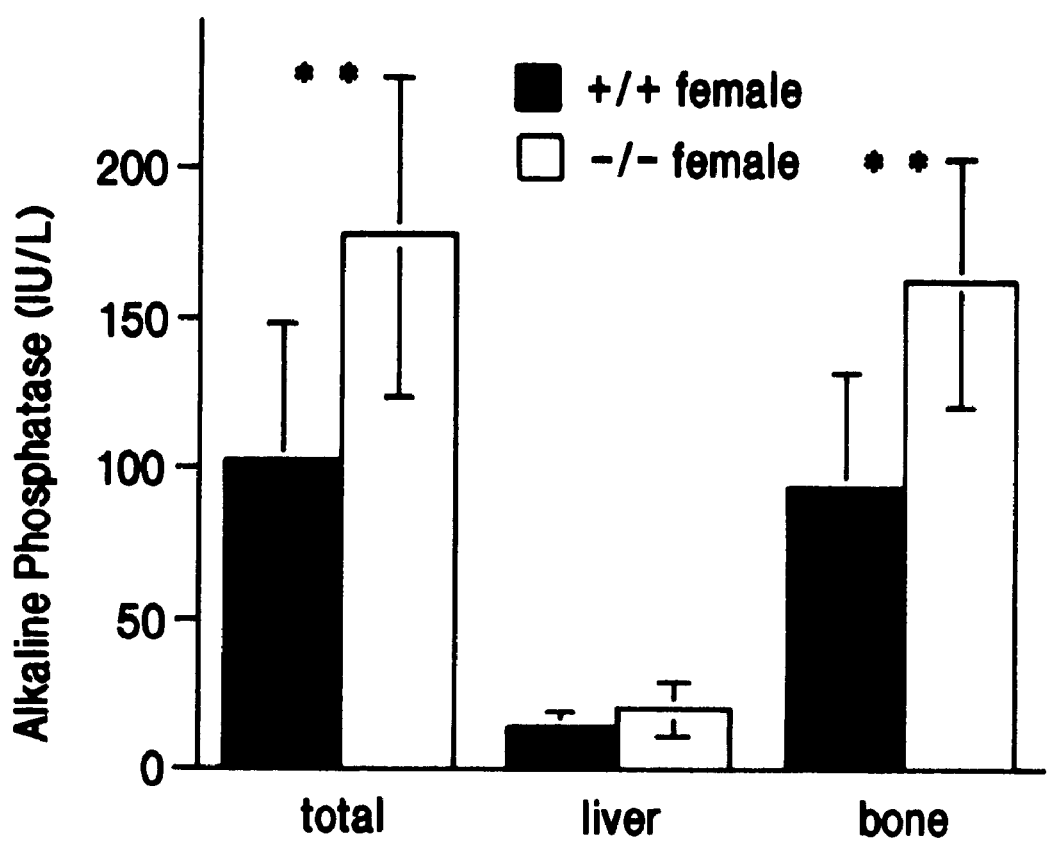
FIG. 4. Analysis of alkaline phosphatase isoenzymes. Serum samples were collected from 14–16 week-old female mice. Total serum alkaline phosphatase activity was assayed by hydrolysis of p-nitrophenylphosphate at pH 9.2, McComb, R. B., Bowers, Jr., G. N., Posen, S. in Alkaline Phosphatase, Plenum Press, New York, 1979. Determination of activity from isoenzymes was based on a quantitative assay described by Hoffmann W. E., Everds, N., Pignatello, M., and Solter, P. F., *Toxicol. Pathol.*, 22:633–638, 1994. Data are presented as mean±SD from 8 wild-type (filled bars) and 14 hepsin–/– (open bars) mice. Statistical differences are indicated by asterisks, $**P<0.01$ by Student's t test.

Blood Chemistry Analysis for Liver Function:

In addition to blood coagulation, hepsin was reported to be required for growth of hepatocytes in vitro Torres-Rosado, A., O'Shea, K. S., Tsuj,i, A., Chou, S.-H., & Kurachi, K. (1993) Proc. Natl. Acad. Sci. USA 90, 7181–7185. To examine the effects of hepsin deficiency on liver function, blood samples from hepsin-deficient mice were analysed. As shown in Table 2, serum concentrations of alanine aminotransferase (SGPT), g-glutamyltranspeptidase (GGT), bilirubin, albumin, globulin, and total protein were similar in hepsin-/- and wild-type mice, and values were within the normal ranges. Interestingly, serum alkaline phosphatase levels were approximately 2-fold higher in hepsin-/- mice when compared to wild-type litter mates (FIG. 3). The elevation of serum alkaline phosphatase was found in both male and female hepsin-/- mice at different ages (FIG. 3). Alkaline phosphatase isoenzymes were analyzed, and results indicated that the elevated alkaline phosphatase in the serum from hepsin-/- mice was mostly of bone origin (FIG. 4).

Morphologic and Histologic Analyses:

Necropsies and histologic examinations were performed on hepsin-/- mice at various ages. No gross abnormalities were indentified in major organs including liver, brain, lung, heart, kidney, pancreas, spleen and bone. Livers from hepsin-/- and wild-type mice appeared similar and had comparable weights (Table 2). In hemtoxylin/eosin-stained sections including liver and bone from hepsin-/- mice were histologically indistinguishable from those of wild-type mice (data not shown). X-ray examinations were also performed to detect potential defects in the skeleton. No structural abnormalities were found in long bones, pelvis and vertebrae in hepsin-/- mice at the age of 5 months (data not shown).

Summary of Results

Human recombinant hepsin expressed on the surface of BHK cells has been reported to specifically activate FVII, Kazama, Y., Hamamoto, T., Foster, D. C., and Kisiel, W., *J. Biol. Chem.*, 270:66–72 (1995), an essential enzyme that acts early in the tissue factor-dependent coagulation pathway, Wildgoose, P., & Kisiel, W., *Blood*, 73:1888–1895 (1989). This finding was confirmed in our own studies (data not shown), indicating a function of hepsin in the initiation of blood coagulation. Genetic and site-directed mutagenesis studies show that the activation cleavage of the Age152-Ile peptide bond in FVII is required to convert the zymogen to an active enzyme, Broze, G. J., & Leykam, J. E., Schwartz, B. D., and Miletich, J. P., *J. Biol. Chem.*, 260:10917–10920 and Wildgoose, P. & Kisiel, W., *Blood*, 73:1888–1895, 1989. The mechanism of FVII activation under physiological conditions is not completely understood. In addition to hepsin, factors IXa, Xa and XIIa and thrombin have been reported to activate FVII in vitro, Kisiel, W., Fujikawa, K., Davie, E. W., *Biochemistry*, 16:4189–4194 (1977); Radcliffe, R., Bagdasarian, A., Colman, R., Nemerson, Y., *Blood*, 50:611–617 (1977); Broze, G. J., Leykam, J. E., Schwartz, B. D., Miletich, J. P., *J. Biol. Chem.*, 260:10917–10920 (1985); Wildgoose, P., Nemerson, Y., Hansen, L. L., Nielsen, F. E., Glazer, S., and Hedner, U., *Blood*, 80:25–28 (1992); and Eichinger, S., Mannucci, P. M., Tradati, F., Arbini, A. A., Rosenberg, T. D., and Bauer, K. A., *Blood*, 86:3021–3025 (1995). Recent studies with haemophilia patients suggest that FIXa is primarily responsible for the basal levels of FVIIa in vivo, Miller, G., Martin, J. C., Mitropoulos, K. A., Esmouf, M. P., Cooper, J. A., Morrissey, J. H., Howarth, D. J., and Tuddenham, E. G. D., *Blood*, 87:4187–4196 (1996); Neuenschwander, P. F. and Morrissey, J. H., *J. Biol. Chem.*, 267:14477–14482 (1992); Morrissey, J. H., Macik, G., Neuenschwander, P. F. and Company, P. C., *Blood*, 81:734–744 (1993); Fenton, J. W., *Ann. N.Y. Acad. Sci.*, 485:5–15 (1986); Nakamura, T., Nishizawa, T., Hagiya, M., Seki, T., Shimonishi, M., Sugimura, A., Tashiro, K., and Shimizu, S., *Nature*, 342:440–443 (1989); Manfioletti, G., Brancolini, C., Avanzi, G., and Schneider, C., *Mol. Cell. Biol.*, 13:4976–4985 (1993). A hepsin knock-out mice in accordance with the present invention is useful to study the above-mentioned pathway, e.g., by preparing animals homozygous or heterozygous for the hepsin knock-out in combination with one or more mutations in any of the above-mentioned genes.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

TABLE 1

Functional hemostatis assays in wild-type and hepsin-deficient mice.

|  | Hepsin+/+ | Hepsin-/- |
|---|---|---|
| Tail bleeding time (sec.) | 70.6 ± 19.7 | 77.3 ± 28.7 |
|  | (n = 5) | (n = 7) |
| PT (sec.) | 20.9 ± 6.6 | 22.6 ± 4.5 |
|  | (n = 6) | (n = 5) |
| aPTT (sec.) | 37.2 ± 11.2 | 38.4 ± 9.1 |
|  | (n = 9) | (n = 6) |
| Thromboplastin-induced DIC: |  |  |
| cessation of breathing (min.) | 1.30 ± 0.16 | 1.42 ± 0.42 |
|  | (n = 5) | (n = 6) |
| cessation of heart beating (min.) | 1.86 ± 0.34 | 1.97 ± 0.45 |
|  | (n = 5) | (n = 6) |

The tail bleeding time, plasma prothrombin time (PT) and activated partial thromboplastin time (aPTT) were performed with 9–12 weeks old mice, as described under "Materials and Methods." In the thromboplastin-induced DIC model, acute death was ascertained as cessation of either breathing or heart beating. Data are presented as mean±SD and the number of mice in each experimental group is indicated in parentheses.

TABLE 2

Liver weight and blood chemistry analysis for liver function.

|  | Hepsin+/+ | Hepsin−/− |
|---|---|---|
| Liver weight (g) | 0.96 ± 0.13 (n = 6) | 0.92 ± 0.08 (n = 5) |
| SGPT (IU/L) | 25.75 ± 8.27 (n = 28) | 31.38 ± 7.86 (n = 29) |
| GGT (IU/L) | 0.71 ± 0.75 (n = 7) | 1.0 ± 0.58 (n = 7) |
| Total protein (g/dl) | 5.48 ± 0.28 (n = 18) | 4.87 ± 0.43 (n = 13) |
| Albumin (g/dl) | 2.81 ± 0.24 (n = 18) | 2.32 ± 0.15 (n = 13) |
| Globulin (g/dl) | 2.67 ± 0.22 (n = 18) | 2.55 ± 0.31 (n = 13) |
| Total bilirubin (mg/dl) | 0.17 ± 0.07 (n = 14) | 0.13 ± 0.07 (n = 11) |

Wild-type and hepsin−/− mice (8–12 weeks old) were sacrificed under $CO_2$, narcosis. The liver was dissected out and weighed. Blood chemistry analysis was performed as described under "Materials and Methods." Data are presented as mean±SD and the number of mice in each experimental group is indicated in parentheses.

---

What is claimed:

1. An isolated nucleic acid molecule comprising a hepsin targeting construct comprising a first selectable marker sequence flanked by DNA sequences homologous to the mouse hepsin gene, wherein when said construct is introduced into a mouse or an ancestor of said mouse at an embryonic stage, said first selectable maker sequence disrupts the endogenous hepsin gene in the genome of said mouse such that said mouse exhibits elevated blood serum alkaline phosphatase levels as compared to a wild-type mouse.

2. The isolated nucleic acid molecule of claim 1, further comprising a second selectable marker sequence, wherein said second selectable marker sequence is located 5' to the 5' DNA sequences homologous to the mouse hepsin gene, or 3' to the 3' DNA sequences homologous to the mouse hepsin gene.

3. The isolated nucleic acid molecule of claim 1, wherein said first selectable marker sequence confers a positive selection characteristic.

4. The isolated nucleic acid molecule of claim 1, wherein said first selectable marker sequence is the neomycin resistance gene.

5. The isolated nucleic acid molecule of claim 2, wherein said second selectable marker sequence confers a negative selection characteristic.

6. The isolated nucleic acid molecule of claim 2, wherein said second selectable marker sequence is the thymidine kinase gene.

7. A vector comprising the nucleic acid of claim 1.

8. A vector comprising the nucleic acid of claim 2.

9. The isolated nucleic acid molecule of claim 1, wherein said DNA sequences homologous to the mouse hepsin gene which are 5' to said first selectable marker sequence, comprise all or part of exons 9–12 of the mouse hepsin gene, and wherein said DNA sequences homologous to the mouse hepsin gene which are 3' to said first selectable marker sequence, comprise exon 4 of the mouse hepsin gene.

10. The isolated nucleic acid molecule of claim 1, wherein said hepsin targeting construct disrupts said mouse hepsin gene by replacing exons 5–8 of the mouse hepsin gene with the first selectable marker sequence.

11. An isolated mouse embryonic stem cell comprising the nucleic acid molecule of claim 1.

12. A transgenic mouse whose genome comprises a homozygous disruption of the endogenous hepsin gene, wherein said disruption comprises the insertion of a selectable marker sequence, and wherein said disruption results in said mouse exhibiting elevated blood serum alkaline phosphatase levels as compared to a wild-type mouse.

13. The transgenic mouse of claim 12, wherein said disruption comprises the replacement of exons 5–8 of the endogenous hepsin gene with said selectable marker sequence.

14. A method for producing a transgenic mouse exhibiting elevated blood serum alkaline phosphatase levels, said method comprising:

(a) introducing a hepsin targeting construct comprising a selectable marker sequence into a mouse embryonic stem cell;

(b) introducing said mouse embryonic stem cell into a mouse embryo;

(c) transplanting said embryo into a pseudopregnant mouse;

(d) allowing said embryo to develop to term; and (e) identifying a transgenic mouse whose genome comprises a disruption of the endogenous hepsin gene in at least one allele;

(f) breeding the transgenic mouse of step (e) to obtain a transgenic mouse whose genome comprises a homozygous disruption of the endogenous hepsin gene, wherein said disruption results in said mouse exhibiting elevated blood serum alkaline phosphatase levels as compared to a wild-type mouse.

15. A transgenic mouse produced by the method of claim 14, wherein the genome of said mouse comprises a homozygous disruption of the endogenous hepsin gene, and wherein said disruption results in said mouse exhibiting elevated blood serum alkaline phosphatase levels as compared to a wild-type mouse.

16. An isolated nucleic acid sequence consisting of the nucleotide sequence of SEQ ID NO: 1.

17. An isolated polypeptide consisting of the amino acid sequence of SEQ ID NO: 2.

* * * * *